US00PP32204P3

(12) United States Plant Patent
Post

(10) Patent No.: US PP32,204 P3
(45) Date of Patent: Sep. 15, 2020

(54) ***CHRYSANTHEMUM* PLANT NAMED 'DLFBLAN1'**

(50) Latin Name: ***Chrysanthemum* X *morifolium***
Varietal Denomination: DLFBLAN1

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 16/602,041

(22) Filed: Jul. 25, 2019

(65) Prior Publication Data

US 2020/0053934 P1 Feb. 13, 2020

Related U.S. Application Data

(60) Provisional application No. 62/764,554, filed on Aug. 7, 2018.

(51) Int. Cl.
*A01H 5/02* (2018.01)
*A01H 6/14* (2018.01)

(52) U.S. Cl.
USPC ..... Plt./294
CPC ..... *A01H 6/1424* (2018.05)

(58) Field of Classification Search
USPC ..... Plt./263.1, 284, 286, 294
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Chrysanthemum* plant named 'DLFBLAN1', characterized by its upright plant habit; vigorous growth habit; dark green-colored leaves; uniform and freely flowering habit; strong upright flowering stems with numerous inflorescences; anemone-type inflorescences with white-colored ray florets and yellow green-colored disc florets; excellent postproduction longevity; and relatively tolerant to low and high temperatures.

2 Drawing Sheets

Botanical designation: *Chrysanthemum* X *morifolium*.
Cultivar denomination: 'DLFBLAN1'.

BACKGROUND OF THE INVENTION

The present invention relates to a new and distinct cultivar of *Chrysanthemum* plant, botanically known as *Chrysanthemum* X *morifolium*, commercially grown as a cut flower and hereinafter referred to by the name 'DLFBLAN1'.

The new *Chrysanthemum* plant is a product of a planned breeding program conducted by the Inventor in Maasdijk, The Netherlands. The objective of the breeding program is to create new freely-flowering cut *Chrysanthemum* plants with attractive inflorescences, strong flowering stems and excellent postproduction longevity.

The new *Chrysanthemum* plant originated from a cross-pollination on Mar. 17, 2011 of a proprietary selection of *Chrysanthemum* x *morifolium* identified as code number DB 33767 as the female, or seed, parent with a proprietary selection of *Chrysanthemum* x *morifolium* identified as code number DB 34154 as the male, or pollen, parent. The new *Chrysanthemum* plant was discovered and selected as a single flowering plant from within the progeny of the stated cross-pollination in a controlled greenhouse environment in Maasdijk, The Netherlands on May 25, 2012.

Asexual reproduction of the new *Chrysanthemum* plant by vegetative terminal cuttings since May 25, 2012 has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFBLAN1'. These characteristics in combination distinguish 'DLFBLAN1' as a new and distinct *Chrysanthemum* plant:

1. Upright plant habit; vigorous growth habit.
2. Dark green-colored leaves.
3. Uniform and freely flowering habit.
4. Strong upright flowering stems with numerous inflorescences.
5. Anemone-type inflorescences with white-colored ray florets and yellow green-colored disc florets.
6. Excellent postproduction longevity.
7. Relatively tolerant to low and high temperatures.

Plants of the new *Chrysanthemum* differ from plants of the female parent selection in the following characteristics:

1. Disc florets of plants of the new *Chrysanthemum* are more green in color than disc florets of plants of the female parent selection.
2. Ray floret apices of plants of the new *Chrysanthemum* are more pointed than and not as rounded as ray floret apices of the female parent selection.

Plants of the new *Chrysanthemum* differ from plants of the male parent selection in the following characteristics:

1. Plants of the new *Chrysanthemum* have anemone-type inflorescences whereas plants of the male parent selection have single-type inflorescences.

2. Disc florets of plants of the new *Chrysanthemum* are yellow green in color whereas disc florets of plants of the male parent selection are yellow in color.

Plants of the new *Chrysanthemum* can be compared to plants of *Chrysanthemum* X *morifolium* 'Deliradost', not patented. In side-by-side comparisons plants of the new *Chrysanthemum* differ primarily from plants of 'Deliradost' in the following characteristics:

1. Disc florets of plants of the new *Chrysanthemum* are more green in color than disc florets of plants of 'Deliradost'.
2. Ray floret apices of plants of the new *Chrysanthemum* are more pointed than and not as rounded as ray floret apices of 'Deliradost'.

Plants of the new *Chrysanthemum* can be compared to plants of *Chrysanthemum* X *morifolium* 'DLFCAPO1', not patented. In side-by-side comparisons plants of the new *Chrysanthemum* differ primarily from plants of 'DLFCAPO1' in disc floret color as disc florets of plants of the new *Chrysanthemum* are more green in color than disc florets of plants of 'DLFCAPO1'.

BRIEF DESCRIPTION OF THE PHOTOGRAPHS

The accompanying colored photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'DLFBLAN1' grown as a spray-type.

The photograph on the second sheet comprises close-up views of the lower (top of the photographic sheet) and upper surfaces (bottom of the photographic sheet) of typical inflorescences and leaves of 'DLFBLAN1'.

DETAILED BOTANICAL DESCRIPTION

The aforementioned photographs and following observations and measurements describe plants grown during the spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 22° C., night temperatures ranged from 20° C. to 25° C. and light levels averaged 8 klux. Plants were grown as single-stem plants and were ten weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFBLAN1'.

Parentage:

*Female, or seed, parent.*—Proprietary selection of *Chrysanthemum* X *morifolium* identified as code designation DB 33767, not patented.

*Male, or pollen, parent.*—Proprietary selection of *Chrysanthemum* X *morifolium* identified as code designation DB 34154, not patented.

Propagation:

*Type.*—Terminal vegetative cuttings.

*Time to initiate roots, summer.*—About six days at temperatures about 24° C.

*Time to initiate roots, winter.*—About eight days at temperatures about 22° C.

*Time to produce a rooted young plant, summer.*—About twelve days at temperatures about 24° C.

*Time to produce a rooted young plant, winter.*—About two weeks at temperatures about 22° C.

*Root description.*—Fine, fibrous; typically creamy white in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous anemone-type cut flower that is typically grown as a single stem spray-type; upright plant habit; vigorous growth habit and moderate to rapid growth rate.

*Plant height, soil level to top of foliar plane.*—About 86.3 cm.

*Plant height, soil level to top of inflorescence plane.*—About 88.9 cm.

*Plant diameter (foliar).*—About 20.5 cm.

*Plant diameter (floral).*—About 14.5 cm.

*Flowering stem length.*—About 83.3 cm.

*Flowering stem diameter.*—About 6.5 mm.

*Flowering stem internode length.*—About 2.3 cm.

*Flowering stem strength.*—Strong.

*Flowering stem aspect.*—Erect.

*Flowering stem texture and luster.*—Moderately pubescent; slightly glossy.

*Flowering stem color, developing.*—Close to 144A, at the internodes, close to between 144A and 146A.

*Flowering stem color, developed.*—Close to between 144A and 146A.

*Leaf description.*—Arrangement: Alternate; simple. Length: About 10.5 cm. Width: About 5.8 cm. Shape: Ovate to elliptic. Apex: Short apiculate. Base: Narrowly attenuate. Margin: Palmately lobed, coarsely serrate to dentate; sinuses convergent to parallel and medium in depth. Texture and luster, upper surface: Moderately to densely pubescent, not rugose; moderately velvety; very slightly glossy. Texture and luster, upper surface: Moderately to densely pubescent, prominent venation; moderately velvety; matte. Venation pattern: Pinnate, reticulate. Color: Developing leaves, upper surface: Close to 137A. Developing leaves, lower surface: Close to 146B. Fully developed leaves, upper surface: Close to NN137A; venation, close to 147C. Fully developed leaves, lower surface: Close to 147B; venation, close to 146B. Petioles: Length: About 1.9 cm. Diameter: About 2.75 mm by 3 mm. Strength: Moderately strong. Texture and luster, upper and lower surfaces: Moderately to densely pubescent; moderately glossy. Color, upper surface: Close to 146C; edges, close to 137A. Color, lower surface: Close to 146D; edges, close to 147B. Stipules: Quantity and appearance: Two leafy stipules, opposite, at the petiole attachment to the stem. Length: About 9 mm. Width: About 1.5 cm. Shape: Flabellate. Apex: Incised. Base: Cuneate. Texture and luster, upper surface: Moderately to densely pubescent, not rugose; moderately velvety; very slightly glossy. Texture and luster, upper surface: Moderately to densely pubescent, prominent venation; moderately velvety; matte. Color: Upper surface: Close to NN137A; venation, close to 147C. Lower surface: Close to 147B; venation, close to 146B.

Inflorescence description:

*Appearance*.—Anemone inflorescence form with oblanceolate-shaped ray florets; inflorescences borne perpendicular to peduncles and face mostly upright to outwardly; ray and disc florets develop acropetally on a capitulum.

*Fragrance*.—Faintly fragrant; sweet.

*Flowering response*.—Under natural conditions, plant flower in the autumn/winter in the Northern Hemisphere; at other times of the year, inflorescence initiation and development can be induced under short day/long night conditions (at least 13.5 hours of darkness); plants exposed to two weeks of long day/short night conditions after planting followed by photoinductive short day/long night conditions flower about 70 days later when grown as a spray-type; uniform flowering habit.

*Postproduction longevity*.—Good postproduction longevity; in an interior environment, inflorescences and foliage will maintain good color and substance for about two weeks; inflorescences persistent.

*Quantity of inflorescences*.—Freely flowering habit; when grown as a spray-type, about 21 inflorescences develop per flowering stem.

*Inflorescence size*.—Diameter: About 6.8 cm. Depth (height): About 2.5 cm. Disc diameter: About 1.6 cm.

*Receptacles*.—Height: About 6 mm. Diameter: About 6 mm. Shape: Broadly ovoid. Color: Close to 193A.

*Inflorescence buds*.—Height: About 9 mm. Diameter: About 1.4 cm. Shape: Flattened globular. Texture and luster: Smooth and glabrous; slightly glossy. Color: Close to 143A and 145C; immature ray florets, close to 155C.

*Ray florets*.—Quantity and arrangement: About 44 arranged in about two whorls. Length: About 2.4 cm to 3.5 cm. Width: About 0.8 cm to 1.4 cm. Shape: Oblanceolate; moderately to strongly concave; moderately carinate. Apex: Bluntly acute to obtuse. Base: Attenuate. Margin: Entire; not undulate. Aspect: Initially upright to eventually about 55° to 60° from vertical. Texture and luster, upper surface: Smooth, glabrous; moderately velvety; not rugose; matte. Texture and luster, lower surface: Smooth, glabrous; slightly velvety; not rugose; slightly glossy. Color: When opening, upper surface: Close to NN155D; at the base, close to 144B. When opening, lower surface: Close to NN155C; at the base, close to 144B. Fully opened, upper and lower surfaces: Close to NN155D; at the base, close to 144B; venation, similar to lamina colors; color does not change with development.

*Disc florets*.—Quantity and arrangement: About 160 spirally arranged in about eight whorls at the center of the receptacle. Length: About 1.1 cm. Diameter: About 2.25 mm. Shape: Lower 63.5% fused into a tube; upper 36.5% free. Apex: Bluntly acute. Margin: Entire. Texture and luster, inner and outer surfaces: Smooth, glabrous; not rugose; slightly glossy. Color, when opening, inner and outer surfaces: Apex: Close to 150B. Mid-section: Close to 150D. Base: Close to 154D. Color, fully opened, inner and outer surfaces: Apex: Close to 150D. Mid-section: Close to 155C. Base: Close to 145C.

*Involucral bracts*.—Quantity and arrangement: About 24 arranged in two whorls. Length: About 1.4 cm. Width: About 5 mm. Shape: Oblong to narrowly ovate. Apex: Obtuse. Base: Cuneate. Margin: Entire. Texture and luster, upper surface: Smooth, glabrous; glossy. Texture and luster, lower surface: Smooth, glabrous; slightly glossy. Color, upper surface: Close to 146B; margins, translucent, and close to 157D; apices, close to N199A. Color, lower surface: Close to 137A; margins, translucent, close to 157D; apices, close to N199A.

*Peduncles*.—Length, terminal peduncle: About 5.7 cm. Diameter, terminal peduncle: About 3 mm. Length, third peduncle: About 7.9 cm. Diameter, terminal peduncle: About 3 mm. Strength: Strong. Aspect, terminal peduncle: Mostly upright. Aspect, third peduncle: About 40° from the flowering stem axis. Texture and luster: Densely pubescent; matte. Color: Close to 137B.

*Reproductive organs*.—Androecium: Present on disc florets only. Quantity: About five per floret. Filament length: About 2 mm. Filament color: Close to 157D. Anther size: About 0.5 mm by 1.25 mm. Anther shape: Narrowly oblong. Anther color: Close to 164A. Pollen amount: Scarce. Pollen color: Close to 14B. Gynoecium: Present on both ray and disc florets. Quantity: One per floret. Pistil length: About 5 mm. Style length: About 4 mm. Style color: Close to 145B. Stigma diameter: About 1 mm. Stigma shape: Cleft, decurrent. Stigma color: Close to 153D. Ovary color: Close to 145D.

*Seeds and fruits*.—To date, seed and fruit production have not been observed on plants of the new *Chrysanthemum*.

Pathogen & pest resistance: Plants of the new *Chrysanthemum* have been observed to be resistant to Fusarium Wilt (*Fusarium oxysporum* f sp. *chrysanthemi*). To date, resistance to pests and other pathogens common to *Chrysanthemum* plants has not been observed on plants of the new *Chrysanthemum* grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFBLAN1' as illustrated and described.

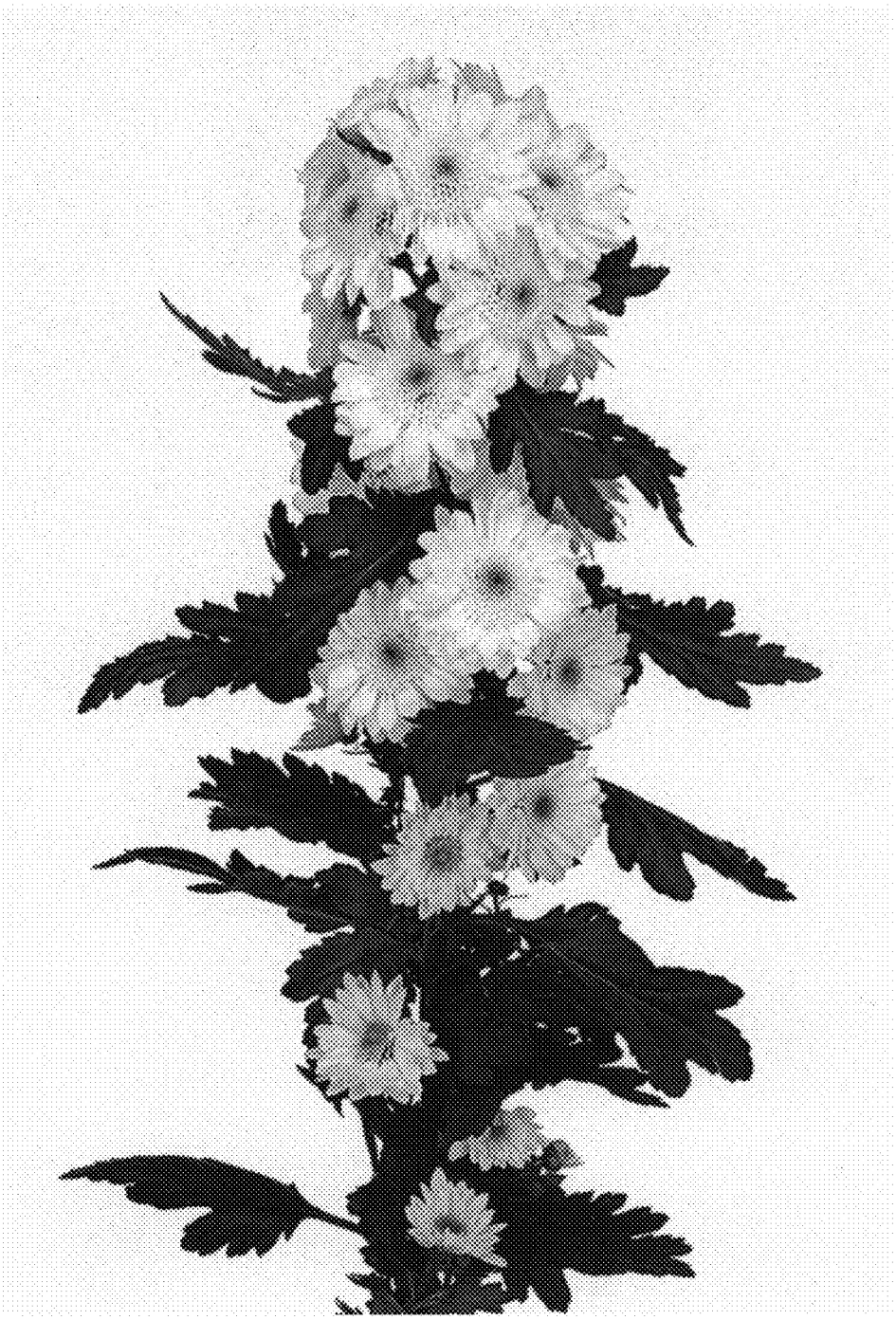

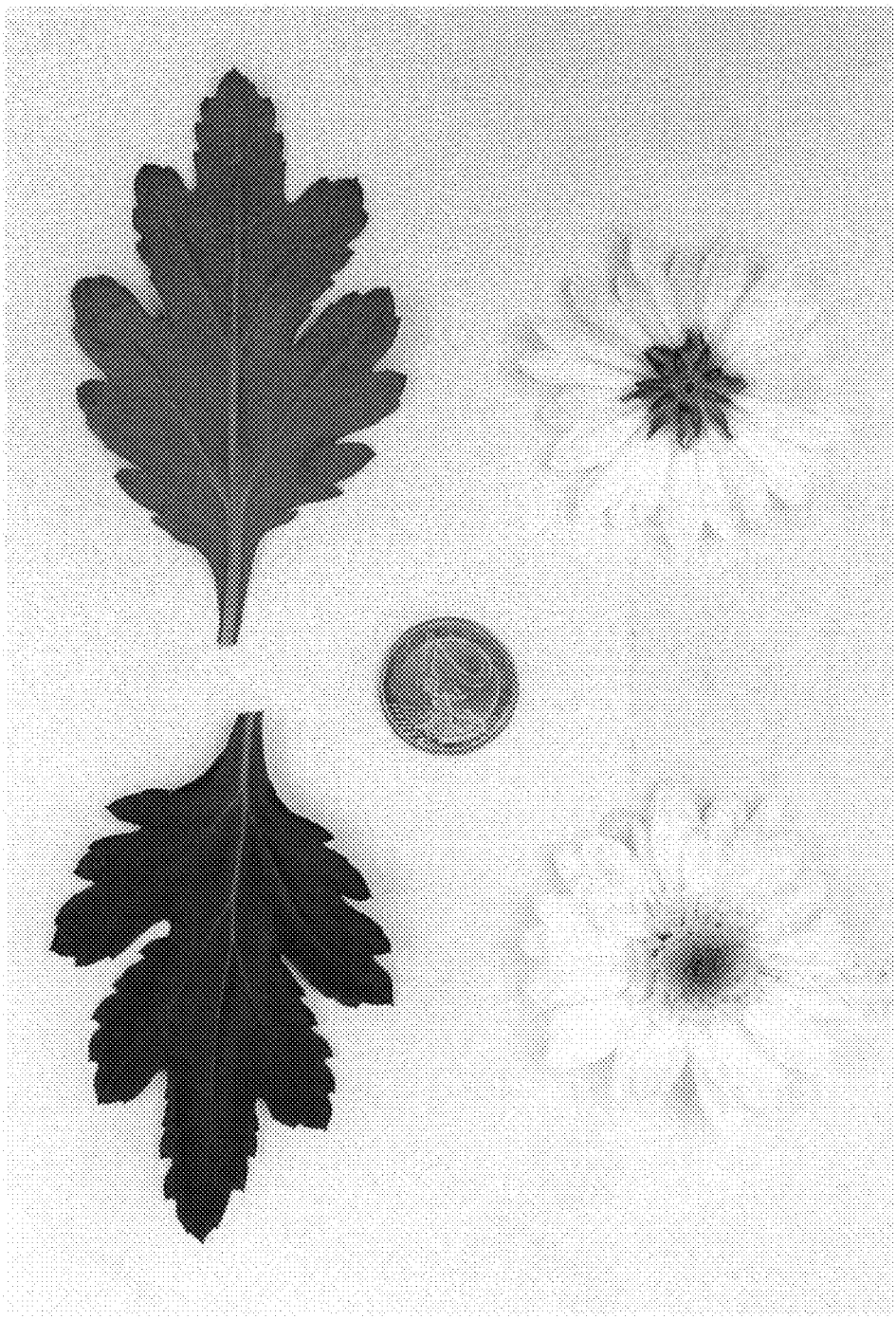

* * * * *